(12) United States Patent
Petrich et al.

(10) Patent No.: US 8,501,113 B2
(45) Date of Patent: Aug. 6, 2013

(54) FLUORESCENCE SPECTROSCOPY IN ABSORBING MEDIA

(75) Inventors: Wolfgang Petrich, Bad Schonborn (DE); Claudia Gaessler-Dietsche, Schriesheim (DE); Carina Horn, Biblis (DE); Kai Hebestreit, Heidelberg (DE); Jean-Michel Asfour, Weinheim (DE); Klemens Bardelang, Burstadt (DE); Gerrit Kocherscheidt, Heidelberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 14 days.

(21) Appl. No.: 12/942,356

(22) Filed: Nov. 9, 2010

(65) Prior Publication Data

US 2011/0064618 A1    Mar. 17, 2011

Related U.S. Application Data

(62) Division of application No. 12/368,286, filed on Feb. 9, 2009, which is a division of application No. 11/585,579, filed on Oct. 24, 2006, now abandoned.

(30) Foreign Application Priority Data

Oct. 25, 2005  (EP) .................................... 05023318

(51) Int. Cl.
*G01N 33/533*    (2006.01)
(52) U.S. Cl.
USPC ..... 422/420; 422/400; 422/82.05; 422/82.08; 436/172
(58) Field of Classification Search
USPC ............. 422/400, 420, 82.05, 82.08; 436/172
See application file for complete search history.

(56) References Cited

U.S. PATENT DOCUMENTS

| | | | |
|---|---|---|---|
| 3,886,045 A * | 5/1975 | Meiattini | ......................... 435/14 |
| 3,992,158 A | 11/1976 | Przbylowicz et al. | |
| 4,547,465 A | 10/1985 | Eikenberry | |

(Continued)

FOREIGN PATENT DOCUMENTS

| AU | 89849/82 | * 10/1982 |
|---|---|---|
| DE | 27 37 290 | 3/1978 |

(Continued)

OTHER PUBLICATIONS

Adeney, M. and Oppenheim, J., A comparison of two physical light blockign agents for sunscreen lotions, UV Instruments at Work, UV-56, Mar. 1992.

(Continued)

*Primary Examiner* — Jill Warden
*Assistant Examiner* — Monique Cole
(74) *Attorney, Agent, or Firm* — Faegre Baker Daniels LLP

(57) ABSTRACT

The invention relates to processes and devices for detecting an analyte in a sample by fluorescence measurement of a fluorophore, wherein the detection medium which contains a fluorophore or a precursor of the fluorophore is admixed with an absorber whose absorbance spectrum superimposes the fluorescence excitation range of the fluorophore. The system consisting of the fluorophore and the absorber, which is produced in the detection medium, has an altered effective fluorescence excitation range with an altered fluorescence excitation maximum. Illumination with fluorescence excitation light can take place within the range of this altered excitation maximum. The measured signal obtained from determining fluorescence emission exhibits only low dependence on the wavelength of the excitation light.

18 Claims, 6 Drawing Sheets

U.S. PATENT DOCUMENTS

| | | | |
|---|---|---|---|
| 6,068,989 | A | 5/2000 | Tanaka et al. |
| 6,576,474 | B2 * | 6/2003 | Wallach .................... 436/169 |
| 6,613,403 | B2 * | 9/2003 | Tan et al. .................... 428/29 |
| 7,341,830 | B2 * | 3/2008 | Horn et al. .................... 435/4 |
| 2002/0137027 | A1 | 9/2002 | Durkop |
| 2005/0214891 | A1 | 9/2005 | Horn et al. |
| 2006/0238757 | A1 | 10/2006 | Silcott |

FOREIGN PATENT DOCUMENTS

| | | | |
|---|---|---|---|
| DE | 2 060 180 | | 4/1981 |
| EP | 0066648 | * | 9/1987 |
| EP | 0 066 648 | | 12/1992 |
| EP | 1 566 637 | | 8/2005 |
| GB | 2060 180 | | 4/1981 |

OTHER PUBLICATIONS

Grant, F.A., Properties of Rutile (Titanium Dioxide), Reviews of Modern Physics, vol. 31, No. 3, Jul. 1959.

Mo, Shang-Di and Ching, W.Y., Electronic and optical properties of three phases of titanium dioxide: Rutile, anatase, and brookite, Physical Review B, vol. 51, No. 19, May 15, 1995-I.

Paul, R.J. and Schneckenburger, H., Oxygen Concentration and the Oxication-Reduction State of Yeast: Determination of Free/Bound NADH and Flavins by Time-Resolved Spectroscopy, Naturwissenschaften 83, 32-35 (1996).

Schneckenburger, Herbert and Konig, Karsten, Fluorescence decay kinetics and imaging of NAD(P)H and flavins as metabolic indicators, Optical Engineering, vol. 31, No. 7, Jul. 1992, p. 1447-1451.

Scott, T. Gordon, Spencer, Richard D., Leonard, Nelson J. and Weber, Gregorio, Emission Properties of NADH. Studies of Fluorescence Lifetimes and Quantum Efficiencies of NADH, AcPyADH, and Simplified Synthetic Models, Contribution from the Department of Chemistry and Chemical Engineering, University of Illinois, Urbana, Illinois 61801.

European Search Report dated Dec. 12, 2005 in EP 0 502 3318.

Schweizerisches Zentrum Fur Qualitatskontrolle, Spektrometrie, Online, Apr. 6, 2005; URL: http://cscq.ch/d/handbuch/programe/speltrometrie.pdf.

Asaihi, R. et al., "Visible-Light Photocatalysis in Nitrogen-Doped Titanium Oxides," Science, Jul. 13, 2001, vol. 293.

Nishimura, Suzushi et al., Standing Wave Enhancement of Red Absorbance and Photocurrent in Dye-Sensitized Titanium Diodixe Photoelectrodes Coupled to Photonic Crystals,: Jounral of the American Chemical Society, May 21, 2003, vol. 125, No. 20, pp. 6306-6310.

Hirayama, Hideki et al., "Shortened Wavelength and Increased Output for Ultraviolet LED Using In A1aN Quaternary Mixed Crystal", Laser Research, vol. 32, No. 6, Jun. 2004, (pp. 402-409)—English translation is also attached.

Schlossman, David (Kobo Products Inc.), Sunscreen Technologies for Foundations and Lipsticks, 8 pages, May 2001.

Ginestar, Jose, Pigments as Photoprotectants, thecosmeticsite.com, Seite 1, von 3, 3 pages, printed Mar. 21, 2005.

* cited by examiner

FLUORESCENCE SPECTROSCOPY IN ABSORBING MEDIA

RELATED APPLICATIONS

This application is a divisional of U.S. patent application Ser. No. 12/368,286, filed Feb. 9, 2009, which is a divisional of U.S. patent application Ser. No. 11/585,579, filed Oct. 24, 2006, now abandoned, which claims the benefits of EP 05023318.8, filed on Oct. 25, 2005, the disclosures of which are herein expressly incorporated by reference for all purposes as if fully set forth herein.

FIELD OF THE INVENTION

The invention relates to processes and devices for detecting an analyte in a sample by fluorescence measurement.

Measurement processes and measuring systems for biochemical analysis are important components of medical diagnostics. Analytes may be determined by measuring the light emitted by a fluorophore. The optimal choice of wavelength of the excitation light required for generating fluorescence plays an important part in making an accurate and reliable determination possible.

The excitation maxima of fluorophores are frequently within the ultraviolet spectral range (UV). Thus, for example, the longest-wavelength excitation maximum of NADH is at 340 nm. Currently, however, there are hardly any inexpensive, battery-powered light sources available for this spectral range, and even those are only in the near UV range.

Currently, light-emitting diodes of notable power (>0.1 mW), as the only inexpensive, narrow-band light source with low power consumption for excitation in the UV range, are industrially available only down to 365 nm, so that excitation can occur only far from the maximum of the excitation range. In addition to the accompanying loss of fluorescence signal, this gives rise to the problem of a very sensitive change in excitation efficiency as a function of the wavelength of the LED, since excitation takes place on the shoulder of the longest-wavelength absorbance peak. Thus, for example, the signal change to be expected for NADH is −5% per nm compared to excitation at 340 nm. In order to guarantee a technical signal stability of 1% for example, the wavelength of the LED would conversely have to remain stable within 0.2 nm, and this would be accomplished only with extreme complexity owing to power fluctuations, temperature dependence and ageing of the LED. Thus the requirement of sufficient wavelength stability would permit merely a very small interval for the allowed temperature range or, alternatively, necessitate incorporation of an active temperature control into a measuring system, but this would not be practicable owing to production costs and power consumption.

U.S. Pat. No. 4,547,465 describes a test element for analysing or transporting liquids, which comprises a porous zone consisting of a polymer with particulate material, for example pigments, dispersed therein. However, there is no indication whatsoever of an improvement in the accuracy of fluorescence measurements.

EP-A-0 066 648 relates to a multi-layer element for determining analytes in an aqueous medium, which element comprises a detection element with a detection layer and a reaction layer, the latter comprising a fibrous, porous and swellable medium. The element may furthermore have a light protection layer which contains particulate pigments. However, there is no indication whatsoever of an improvement in the accuracy of fluorescence determinations.

US 2002/0137027 relates to a process for determining hydrogen peroxide generated by an oxidase by means of a lanthanoid-ligand complex. Fluorescence is excited at a wavelength of preferably 330-415 nm and emission is detected at 600-630 nm.

U.S. Pat. No. 3,992,158 describes a test element for use in the analysis of liquids. The test element may contain one or more reflection layers which contain pigments such as titanium dioxide and barium sulphate, for example, as absorbers. This reflection layer is separated in space from the layer of the test element, which contains the detection reagents. There is furthermore no indication whatsoever of an improvement in the accuracy of fluorescence measurements.

SUMMARY OF THE INVENTION

The present invention provides a process for detecting an analyte by fluorescence measurement, the process having a reduced dependence of the measured signal on the excitation wavelength. The solution according to the invention is to provide a process or system for detecting an analyte in a sample by fluorescence measurement of a fluorophore, wherein the detection medium which contains a fluorophore or a precursor of the fluorophore is admixed with an absorber whose absorbance spectrum superimposes the fluorescence excitation range of the fluorophore. The system consisting of the fluorophore and the absorber, which is produced in the detection medium, has an altered effective fluorescence excitation range with an altered fluorescence excitation maximum. Illumination with fluorescence excitation light can take place within the range of this altered excitation maximum. The measured signal obtained from determining fluorescence emission exhibits only low dependence on the wavelength of the excitation light. Owing to the altered wavelength of the excitation light, it is furthermore also possible to employ inexpensive light sources such as UV LEDs for example.

In a first aspect, the present invention relates to a process for detecting an analyte in a sample by fluorescence measurement, comprising the following steps:
(a) providing a detection medium comprising:
  (i) at least part of the sample in which the analyte is to be detected,
  (ii) one of a fluorophore which has an excitation range with at least one excitation maximum at a first wavelength, and a fluorophore precursor from which the fluorophore can be produced in the presence of the sample; and
  (iii) an absorber which absorbs light over a part of the excitation range of the fluorophore, resulting in an altered effective excitation range of the system consisting of the fluorophore and the absorber with an excitation maximum at a second wavelength which differs from the first wavelength,
(b) illuminating the detection medium with light in order to excite the fluorophore in the region of the second wavelength, and
(c) determining a fluorescence emission of the fluorophore at one or more measuring wavelengths to detect one of a presence, an amount and an activity of the analyte in the sample.

In a further aspect, the invention relates to a test element for detecting an analyte, comprising
(i) one of a fluorophore which has an excitation range with at least one excitation maximum at a first wavelength, and a fluorophore precursor from which the fluorophore can be produced; and
(ii) an absorber which absorbs light over a part of the excitation range of the fluorophore wherein the one of the fluorophore and the fluorophore precursor and the absorber are arranged on the test element in such a way that incident light for excitation of the fluorophore hits one of (a) the absorber first and then the fluorophore and (b) the fluorophore and the absorber at substantially the same time, resulting in an altered effective excitation maximum for the system consisting of the fluorophore and the absorber with a second wavelength which differs from the first wavelength.

BRIEF DESCRIPTION OF THE DRAWINGS

The above-mentioned features and aspects of the present invention will be further described and the invention will be better understood with reference to the following drawings.

DETAILED DESCRIPTION OF EMBODIMENTS OF THE INVENTION

The embodiments disclosed below are not intended to be exhaustive or to limit the invention to the precise forms disclosed in the following detailed description. Rather, the embodiments are chosen and described so that others skilled in the art may utilize their teachings.

Figure 1:
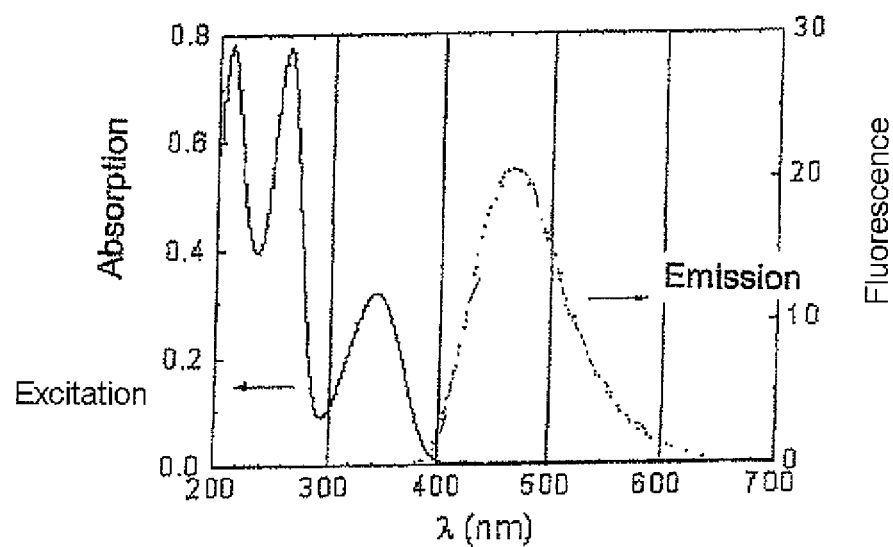
FIG. 1 depicts schematically the excitation and emission spectra of NADH in aqueous solution as a function of the wavelength $\lambda$. There are 3 fluorescence excitation maxima at wavelengths of 210 nm, 260 nm and 340 nm and the emission maximum around 460 nm recognizable.
Figure 2:
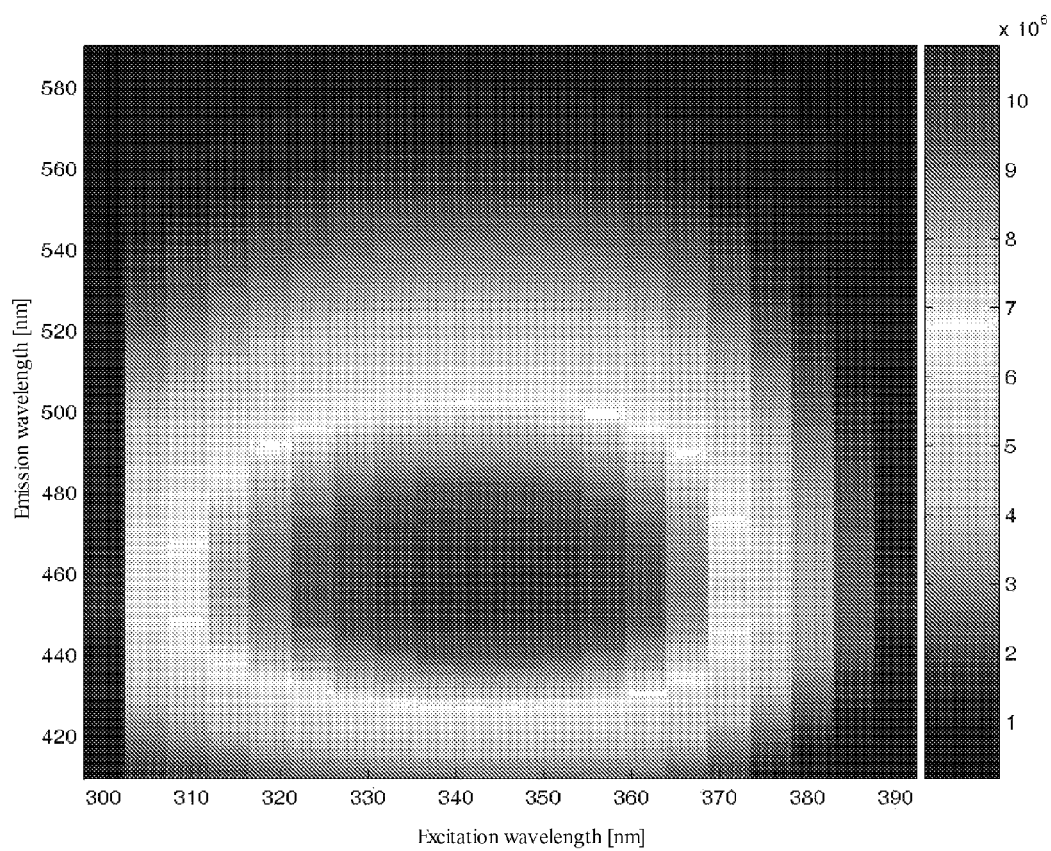
FIG. 2 depicts the excitation-emission matrix of fluorescence excitation of NADH in 50 mM Hepes buffer, pH 7.5. Regions indicated in red (labeled A) correspond to high fluorescence, regions indicated in blue (labeled B) correspond to low fluorescence.
Figure 3:
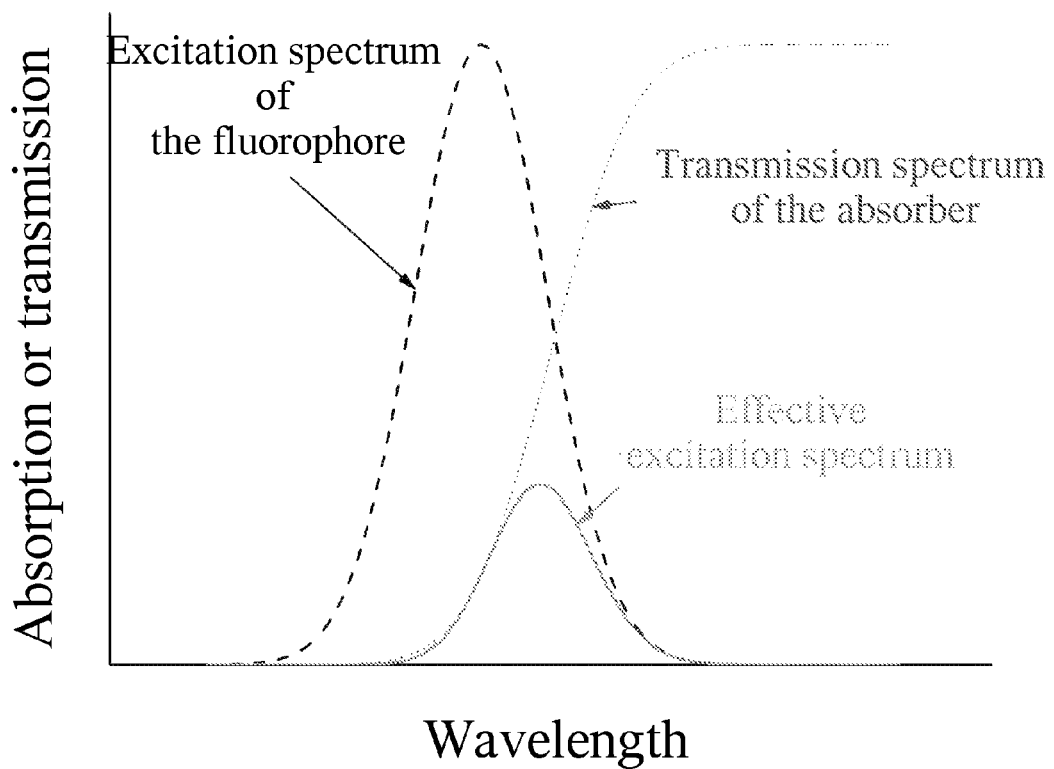
FIG. 3 depicts the scheme of the functional principle of the present invention. Curve 1 depicts the excitation spectrum of a fluorophore in the absence of an absorber. Curve 2 depicts the transmission spectrum of the absorber, which superimposes the excitation range of the fluorophore. Curve 3 is the altered effective excitation range resulting from superimposing the excitation range of the fluorophore and the transmission spectrum of the absorber.
Figure 4:
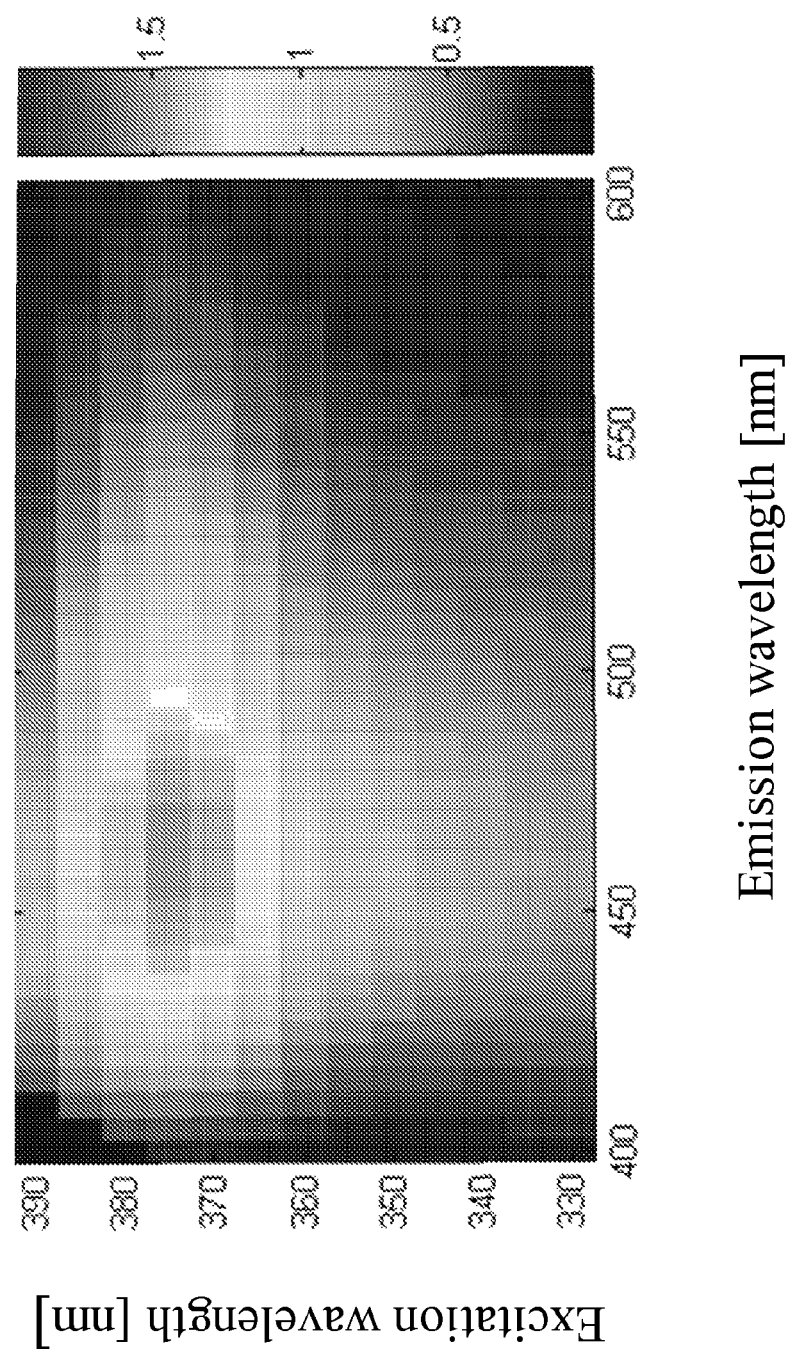
FIG. 4 depicts the excitation-emission matrix, analogous to FIG. 2, for a test element which contains the fluorophore NADH and the absorber $TiO_2$ (rutile, average pigment diameter: 300 nm). Regions of high fluorescence are labeled C, while regions of low fluorescence are labeled D. As can be seen, the maximum of the effective excitation spectrum is within the range of a wavelength of 375 nm for which LEDs are commercially available. The amplitude of the effective excitation spectrum fluctuates in the relevant wavelength range around the excitation maximum by less than 1% per nm.

According to the present invention the term "excitation maximum of the fluorophore" means the wavelength, at which a system consisting of the fluorophore in the absence of the absorber exhibits a maximum of fluorescence excitation. The term "excitation maximum of the system consisting of fluorophore and absorber" means the wavelength, at which a system consisting of a fluorophore and an absorber exhibits a maximum of fluorescence excitation. The term "effective excitation maximum" means the wavelength of the measured maximum of fluorescence excitation of a given system (fluorophore alone or fluorophore and absorber). According to the present invention, systems consisting of fluorophores and absorbers are employed, which exhibit an altered "effective excitation maximum", i.e. an excitation maximum which has shifted compared to the excitation maximum of the fluorophore alone. An example for such a shift of the excitation maximum is shown in FIG. 3.

The process and test element according to the invention may be employed for determining any analytes, for example in the field of clinical diagnostics. The analyte may be determined qualitatively and/or quantitatively. Preference is given to quantitative determination of the analyte, i.e. the amount, concentration or activity of the analyte in the sample to be examined is quantitatively determined by fluorescence measurement.

Analytes which may be determined by the process and test element according to the invention are any biological or chemical substances which can be detected by fluorescence measurement. If required, suitable detection regents may be employed here in the process or the test element, in addition to the fluorophore or the fluorophore precursor.

Preferably, the analyte is a substance determinable by one or more enzymatic reactions, for example an enzyme or an enzyme substrate. Preferred examples of the analyte are glucosedehydrogenase, lactate dehydrogenase, malate dehydrogenase, glycerol dehydrogenase, alcohol dehydrogenase, α-hydroxybutyrate dehydrogenase, sorbitol dehydrogenase, amino acid dehydrogenase, glucose, lactic acid, maleic acid, glycerol, alcohol, cholesterol, triglycerides, lipoproteins such as LDL or HDL, ascorbic acid, cysteine, glutathione, peptides, uric acid, urea, ammonium, salicylate, pyruvate, 5'-nucleotidase, creatine kinase (CK), lactate dehydrogenase (LDH) and carbon dioxide etc.

When detecting enzyme substrates, the detection reagents preferably contain one or more enzymes suitable for detecting the substrate. Examples of suitable enzymes are dehydrogenases selected from a glucose dehydrogenase (E.C.1.1.1.47), lactate dehydrogenase (E.C.1.1.1.27, 1.1.1.28), malate dehydrogenase (E.C.1.1.1.37), glycerol dehydrogenase (E.C.1.1.1.6), alcohol dehydrogenase (E.C.1.1.1.1) α-hydroxybutyrate dehydrogenase, sorbitol dehydrogenase or amino acid dehydrogenase, for example L-amino acid dehydrogenase (E.C.1.4.1.5). Further suitable enzymes are oxidases such as, for example, glucose oxidase (E.C.1.1.3.4) or cholesterol oxidase (E.C.1.1.3.6) and amino transferases such as, for example, aspartate or alanine amino transferase, 5'-nucleotidase or creatine kinase.

Particular preference is given to detecting glucose, the detection reagent comprising in particular glucose dehydrogenase.

When detecting enzymes, the detection reagents preferably contain one or more substrates suitable for detecting the enzyme.

Further components of detection reagents may be customary buffers, auxiliary substances or additives.

The starting material employed in the process or system according to the invention may be the fluorophore itself. Alternatively, it is possible to employ a fluorophore precursor from which a fluorophore whose fluorescence is then determined can be produced in the presence of the sample and the detection reagents.

The fluorophore is a substance which, when illuminated with fluorescence excitation light, produces a measured signal which indicates qualitatively the presence or absence of the analyte in the sample or which correlates with the amount, concentration or activity of the analyte in the sample. For example, the fluorophore itself may be the analyte to be determined or may be produced from the analytes to be determined. Preferably, however, the fluorophore is a substance which is a co-enzyme of an enzymatic reaction by which the analyte is determined. Preferred examples of co-enzymes are nicotin-adenine dinucleotides, such as NADH or NADPH, flavine nucleotides, etc.

Preference is given to using as a fluorophore a substance which has at least one excitation maximum in the UV range, such as NADH or NADPH, for example, or derivatives thereof. Suitable as fluorophores are of course also substances which have excitation maxima in the visible or near IR range.

Preferences is given to using as a fluorescence precursor a substance from which a fluorophore is produced, for example by a chemical reaction such as oxidation, for example. Preferred fluorophore precursors are substances from which fluorophores with at least one excitation maximum in the UV range can be produced, such as NAD or NADP for example or derivatives thereof.

According to the present invention, the detection medium which contains the fluorophore or fluorophore precursor and, where appropriate, at least one other detection reagent is admixed with an absorber whose absorbance/transmission properties for light illuminating in the detection medium change across the excitation range of the fluorophore. Preference is given to using an absorber which absorbs light across a part of the excitation range of the fluorophore and which is substantially transparent for light across another part of the excitation range of the fluorophore.

Particular preference is given to using an absorber which absorbs light within the shorter-wavelength part of the excitation range of the fluorophore and which is substantially transparent within the longer-wavelength part of the excitation range. This results in the effective excitation maximum of the fluorophore being shifted to a longer wavelength in the presence of the absorber. The excitation maximum is shifted preferably by at least 10 nm, particularly preferably by at least 20 nm and more preferably by at least 30 nm, based on the excitation maximum in the absence of the absorber.

Preference is given in the process according to the invention to illuminating with light for excitation of the fluorophore in the range of the altered effective excitation maximum, for example in a range of ±10 nm, in particular ±5 nm, around the wavelength in the excitation maximum of the altered effective excitation range. Thus, when using NADH or NADPH as fluorophore, for example, fluorescence excitation is at a wavelength in the range of preferably 360 nm or higher, in particular 365-380 nm. Fluorescence excitation is carried out using a suitable light source, for example a halogen lamp, a light-emitting diode or a laser diode.

Preference is given to light-emitting or laser diodes which give off light in a wavelength range of 370-390 nm. In this way it is possible to use inexpensive light sources for fluorescence excitation.

In order to enable the excitation maximum of the fluorophore to be shifted as efficiently as possible, use is advantageously made of an absorber which changes relative transmission in the detection medium for incident light across the excitation range of the fluorophore from no more than 20%, preferably no more than 10%, to at least 80% and preferably at least 90%, based on maximum transmission in the detection medium used (transmission in the absence of the absorber). Relative transmission of the detection medium is changed here preferably within a wavelength range of $\leq 100$ nm, particularly preferably $\leq 60$ nm and most preferably $\leq 40$ nm.

Suitable absorbers are any substances which absorb light across a part of the excitation range of the fluorophore and whose presence does not interfere with the detection process.

The absorber is preferably in the form of particles which have a diameter of $\leq 1$ μm, preferably $\leq 500$ nm and particularly preferably of 200-400 nm. The particle size is preferably at least 50 nm. Preferred examples of suitable absorber materials are metal oxides and metal salts such as metal sulphides or metal sulphates for example, in particular oxides of titanium, such as TiO, $TiO_2$, oxides of zirconium, such as $ZrO_2$, oxides or sulphides of zinc, such as ZnO or ZnS, and barium salts such as, for example, BaS or $BaSO_4$, and any combinations thereof. The absorber particularly preferably contains $TiO_2$ which may be in the form of rutile, for example. In principle, pigments which are employed as UV blockers in sun protection creams or other formulations are also suitable for the process according to the invention.

Preference may also be given to using absorber materials which have light-scattering properties so that the fluorescence excitation light is scattered several times in the area of the detection medium and the average path length of the excitation light in the detection medium is increased in order to obtain more efficient excitation.

By varying the absorber material, grain size, crystal structure or/and purity, in particular by adding relatively small amounts of further absorbers, it is possible to vary the position and shape of the absorbance spectrum and thereby also the shape and position of the excitation range of the system consisting of the fluorophore and the absorber.

Figure 5:
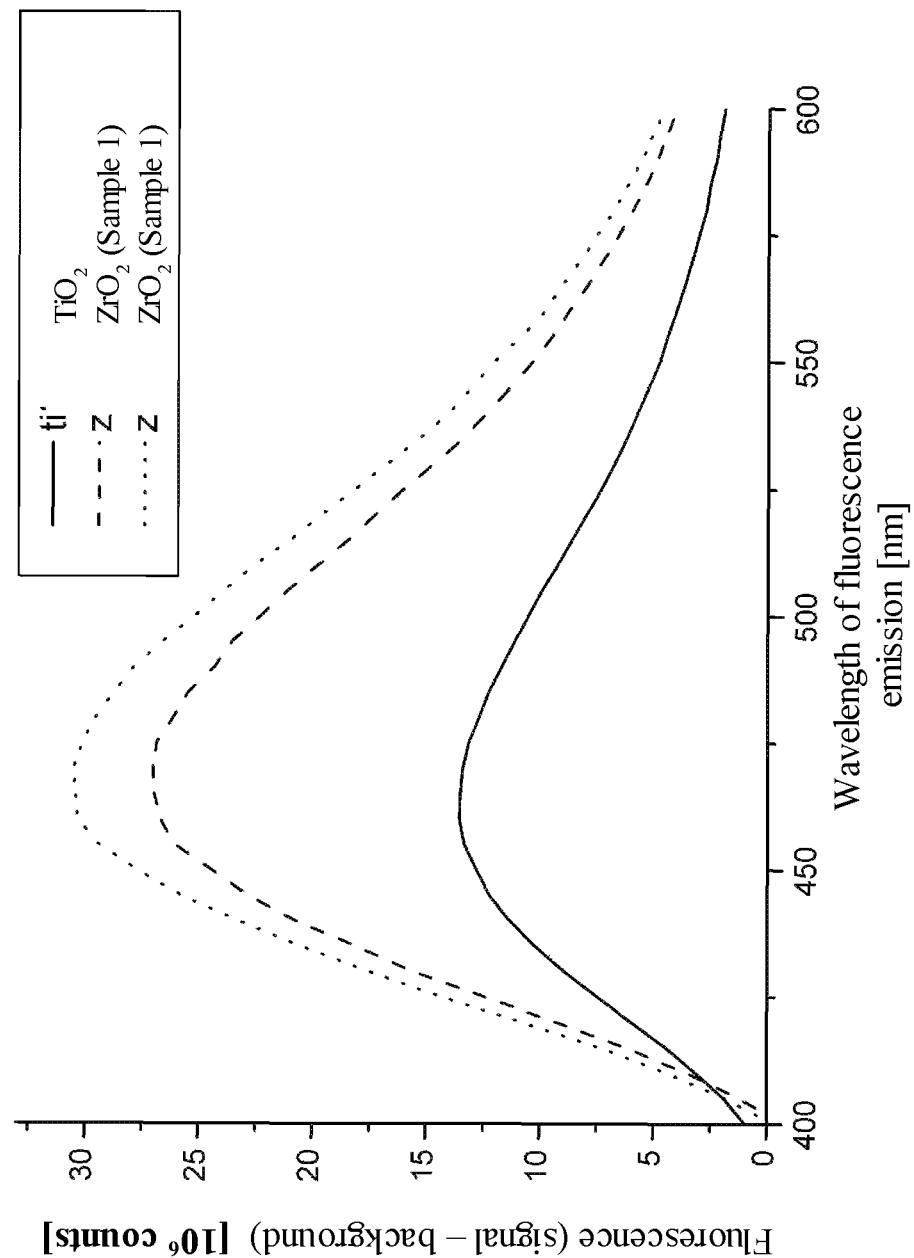
FIG. 5 depicts the emission spectrum of NADH with the use of various absorber ($TiO_2$ and $ZrO_2$ with 2 different particle sizes).
Figure 6:
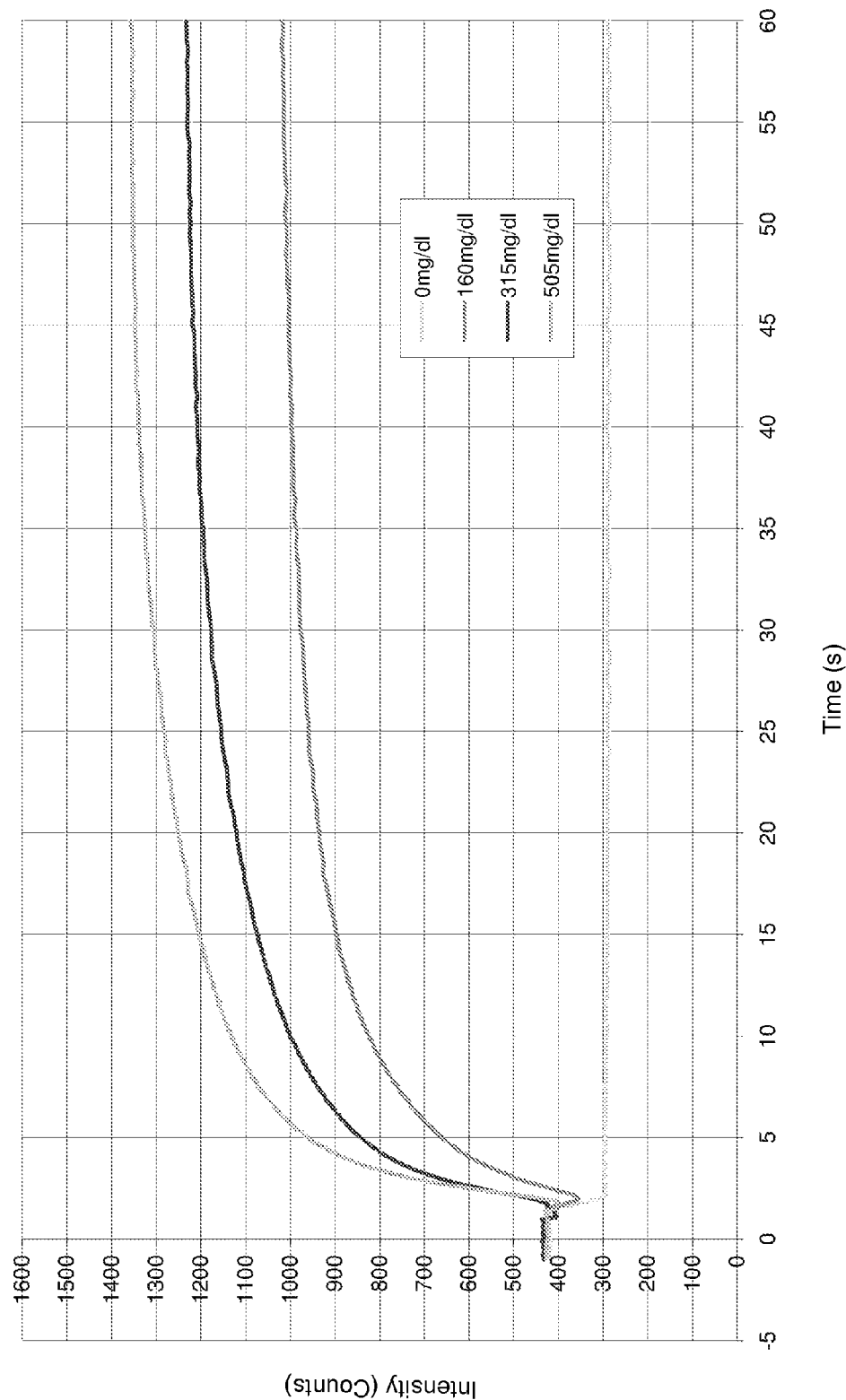
FIG. 6 depicts the NADH fluorescence signals as a function of time. The test layer here consists of a reagent and different amounts of $ZrO_2$. Excitation is at a wavelength of 375 nm and the emitted fluorescence light is observed using a photodiode (BPW34) through an edge filter (plastic composite filter KV418).

A suitable choice of fluorophore or/and absorber enables the slope of the shoulder of the effective excitation range of the system of the fluorophore and the absorber to be varied at the desired wavelength. Thus it is possible, for example, by using $ZrO_2$ as absorber, to shift the absorbance shoulder to shorter wavelengths compared to $TiO_2$. This enables the amplitude of the effective excitation spectrum of fluorophore and absorber to be increased at the desired wavelength, it nevertheless being possible for the slope of the shoulder at this point to be brought within a tolerable range. Thus FIG. 5 depicts the emission spectrum of NADH with the use of $TiO_2$ and $ZrO_2$, respectively. It is furthermore possible to optimize fluorescence yield and slope of the shoulder of the effective absorbance by varying the absorber.

The fluorescence emission of the fluorophore can be determined in the usual way at one or more suitable measuring wavelengths by using suitable detection systems known to the skilled worker. Said determination may thus also be carried out by measuring fluorescence quenching due to, for example, the presence of the analyte.

The process according to the invention can markedly reduce the dependence of the measured signal on the wavelength of the fluorescence excitation light. Preference is given to achieving a signal stability of <1% per nm of change in the fluorescence excitation wavelength.

The process may be carried out in the form of a liquid assay, it being possible for the fluorophore or fluorophore precursor, where appropriate at least one further reagent and the absorber to be present in the form of a suspension in an aqueous or non-aqueous liquid or as a powder. Preference is given to carrying out the process as a dry assay, with the reagent being applied to a test element. The test element may comprise, for example, a test strip or a test tape of absorbent or/and swellable material, to which the sample to be examined is applied. Suitable materials may be selected, for example, from the group of celluloses, plastic materials etc. Other preferred examples of test elements are integrated measuring systems, for example those which comprise a sampling element, such as a needle or lancet, integrated in measuring equipment and, where appropriate, equipment for sample transport. The test element may have one or more layers comprising the detection reagents, the absorber and the fluorophore or fluorophore precursor. Preference is given here to the fluorophore or fluorophore precursor and the absorber being arranged on the test element in such a way that incident light for excitation of the fluorophore first hits the absorber and then the fluorophore or said fluorophore and absorber at the same time. Preference is given to arranging the fluorophore or fluorophore precursor and the absorber in one layer on the test element. U.S. Pat. No. 7,238,534 describes preferred test strips. U.S. Publication No. 2005/0201897 describes preferred examples of designing the test element as a test tape, i.e. as a test element which comprises a variety of test strips, with U.S. Pat. No. 7,288,073 and U.S. Publication No. 2006/0229533 disclosing preferred examples of integrated measuring systems. Alternatively, the detection reagent may also be embedded in a gel matrix (see, for example, DE 102 21 845). Reference is explicitly made to the disclosure of the abovementioned documents. Each of U.S. Pat. No. 7,238,534, U.S. Publication No. 2005/0201897, U.S. Pat. No. 7,288,073 and U.S. Publication No. 2006/0229533 are hereby expressly incorporated herein by reference. Particular preference is given to a procedure in which the fluorophore and the absorber together are present in one phase or one layer, for example on a test element, prior to applying the sample.

The sample to be examined is usually a liquid sample, in particular a body fluid such as blood, plasma, serum, saliva or urine. Particular preference is given to determining glucose in blood.

The invention furthermore relates to a novel test element for detecting an analyte, which comprises a fluorophore, an absorber and, where appropriate, detection reagents, with these components being arranged on the test element in such a way that incident light for excitation of the fluorophore first hits the absorber and then the fluorophore or hits the fluorophore and absorber essentially at the same time. Preference is given to arranging said components in such a way that they are present in one phase or one layer on the test element prior to applying the sample.

The test element is preferably designed in the form of a test strip, test tape or integrated measuring system. It may be employed in a process for detecting an analyte in a sample, which comprises the steps:
(a) contacting the test element with the sample,
(b) illuminating with light for excitation of the fluorophore in the region of a wavelength which is within the range of the altered effective excitation maximum of fluorophore plus absorber, and
(c) determining the fluorescence emission of the fluorophore at a suitable measuring wavelength to detect the presence and the amount or activity of the analyte in the sample.

A further subject matter still is the use of an absorber, as explained above, in a test element for modifying the fluorescence excitation maximum of a fluorophore, in particular in a process for determining analytes in a sample.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

The invention claimed is:

1. A test element for detecting an analyte within a sample, comprising:
   (i) a detection reagent;
   (ii) a fluorophore precursor which, in the presence of the sample and the detection reagent, produces a fluorophore having an excitation range with at least one excitation maximum at a first wavelength; and
   (iii) an absorber which absorbs light over a part of the excitation range of the fluorophore,
      wherein the test element is arranged in such a way that incident light for excitation of the fluorophore produced by the fluorophore precursor first hits the absorber and then the fluorophore or hits the fluorophore and the absorber essentially at the same time, resulting in an altered effective excitation maximum for a combination of the fluorophore and the absorber with a second wavelength which differs from the first wavelength.

2. The test element according to claim 1, which is in the form of one of a test strip, a test tape and an integrated measuring system.

3. The test element according to claim 1 in a process for detecting an analyte in a sample, comprising the following steps:
   (a) contacting the test element with the sample,
   (b) illuminating with light in order to excite the produced fluorophore in the region of the second wavelength, and
   (c) determining the fluorescence emission of the fluorophore at a suitable measuring wavelength to detect the presence, the amount or activity of the analyte in the sample.

4. A test element for detecting an analyte, comprising:
   (i) a fluorophore which has an excitation range with at least one excitation maximum at a first wavelength, or a fluorophore precursor from which the fluorophore can be produced in the presence of the sample;
   (ii) an absorber which absorbs light over a part of the excitation range of the fluorophore (i), and
   (iii) at least one reagent for detecting an analyte,
      wherein the fluorophore or the fluorophore precursor (i) and absorber (ii) are arranged on the test element in such a way that incident light for excitation of the fluorophore first hits the absorber and then the fluorophore resulting in an altered effective excitation maximum for a combination of the fluorophore (i) and the absorber (ii) at a second wavelength which differs from the first wavelength.

5. The test element according to claim 4, which is in the form of one of a test strip, a test tape and an integrated measuring system.

6. The test element according to claim 4 in a process for detecting an analyte in a sample, comprising the following steps:
   (a) contacting the test element with the sample,
   (b) illuminating with light in order to excite the produced fluorophore in the region of the second wavelength, and
   (c) determining the fluorescence emission of the fluorophore at a suitable measuring wavelength to detect the presence, the amount or activity of the analyte in the sample.

7. The test element according to claim 4, wherein the absorber comprises at least one of TiO, $TiO_2$, $ZrO_2$, ZnO, ZnS, BaS, and $BaSO_4$.

8. The test element according to claim 4, wherein the at least one reagent for detecting an analyte (iii), the fluorophore or the fluorophore precursor (i), and the absorber (ii) each comprise a powder, the powders of the at least one reagent for detecting an analyte (iii), the fluorophore or the fluorophore precursor (i), and the absorber (ii) being applied to the test element in a plurality of layers, the powders of the fluorophore or the fluorophore precursor (i) and the absorber (ii) comprising a first layer and the powder of the at least one reagent for detecting an analyte (iii) comprising a second layer.

9. The test element according to claim 4, wherein the first and second wavelengths differ by at least 20 nm.

10. The test element according to claim 1, wherein the fluorophore precursor is a co-enzyme, which in the presence of the detection reagent and the sample undergoes an enzymatic reaction thereby producing the fluorophore.

11. The test element according to claim 10, which is in the form of one of a test strip, a test tape and an integrated measuring system.

12. The test element according to claim 10 in a process for detecting an analyte in a sample, comprising the following steps:
(a) contacting the test element with the sample,
(b) illuminating with light in order to excite the produced fluorophore in the region of the second wavelength, and
(c) determining the fluorescence emission of the fluorophore at a suitable measuring wavelength to detect the presence, the amount or activity of the analyte in the sample.

13. The test element according to claim 10, wherein the absorber comprises at least one of $TiO$, $TiO_2$, $ZrO_2$, $ZnO$, $ZnS$, $BaS$, and $BaSO_4$.

14. The test element according to claim 10, wherein the detection reagent, the co-enzyme, and the absorber each comprise a powder, the powders of the detection reagent, the co-enzyme, and the absorber being applied to the test element in a plurality of layers, the powders of the fluorophore precursor and the absorber comprising a first layer and the powder of the detection reagent comprising a second layer.

15. The test element according to claim 10, wherein the first and second wavelengths differ by at least 20 nm.

16. The test element according to claim 1, wherein the absorber comprises at least one of $TiO$, $TiO_2$, $ZrO_2$, $ZnO$, $ZnS$, $BaS$, and $BaSO_4$.

17. The test element according to claim 1, wherein the detection reagent, the fluorophore precursor, and the absorber each comprise a powder, the powders of the detection reagent, the fluorophore precursor, and the absorber being applied to the test element in a plurality of layers, the powders of the fluorophore precursor and the absorber comprising a first layer and the powder of the detection reagent comprising a second layer.

18. The test element according to claim 1, wherein the first and second wavelengths differ by at least 20 nm.

* * * * *